United States Patent [19]

Jouquey et al.

[11] Patent Number: 4,565,876

[45] Date of Patent: Jan. 21, 1986

[54] PROCESS

[75] Inventors: Alain Jouquey, Paris; Peter F. Hunt, Gonesse, both of France

[73] Assignee: Roussel Uclaf, Paris, France

[21] Appl. No.: 612,606

[22] Filed: May 21, 1984

[30] Foreign Application Priority Data

Jun. 20, 1983 [FR] France ................................ 83 10141

[51] Int. Cl.⁴ ........................................... C07D 209/56
[52] U.S. Cl. ..................................... 548/426; 260/464
[58] Field of Search ................ 548/420, 426; 260/464

[56] References Cited

U.S. PATENT DOCUMENTS

| | | | |
|---|---|---|---|
| 3,257,412 | 6/1966 | Baran | 548/426 |
| 3,317,557 | 5/1967 | Kierstead | 548/426 |
| 3,539,588 | 11/1970 | Sallay | 548/420 X |
| 3,634,419 | 1/1972 | Nelson | 548/426 |
| 3,658,880 | 4/1972 | Nelson | 548/426 |

OTHER PUBLICATIONS

Hunt, et al.; Neuropharmacology, 20, pp. 357-361, (1981).

*Primary Examiner*—Joseph Paul Brust
*Attorney, Agent, or Firm*—Bierman, Peroff & Muserlian

[57] ABSTRACT

A novel process for the preparation of a 16-imino-17-aza-steroid of the formula I wherein A is selected from the group consisting of hydrogen and tritium comprising reacting a compound of the formula II wherein A has the above definition and R is an acyl of an organic carboxylic acid of 1 to 8 carbon atoms with an oximation agent to obtain a compound of the formula III reacting the latter with an agent to form an acid chloride to obtain a compound of the formula IV reacting the latter with ammonia to obtain a compound of the formula V reacting the latter with an alkali metal hypohalite in the presence of a base to obtain a compound of the formula VI wherein X is a halogen and reacting the latter with a base to obtain the desired compound and the novel compound of formula I wherein A is tritium and the novel intermediates of formulae III, IV, V and VI.

6 Claims, No Drawings

PROCESS

STATE OF THE ART

The compound of formula I wherein A is hydrogen is described by Boaventura et al [1978 in Abstracts: VII Congresso Latinoamericano de Farmacologia Sao Paulo and P. Hunt and S. Clements-Jewery: A steroid derivative, R 5135, Antagonizes the GABA/Benzodiazepine receptor interaction. Neuropharmacology Vol. 20, p. 357–361, 1981] and its pharmacological properties are described therein.

OBJECTS OF THE INVENTION

It is an object of the invention to provide a novel process for the preparation of the compounds of formula I and the novel intermediates formed therein.

It is another object of the invention to provide the novel compound of formula I wherein A is tritium.

These and other objects and advantages of the invention will become obvious from the following detailed description.

THE INVENTION

The novel process of the invention for the preparation of a 16-imino-17-aza-steroid of the formula

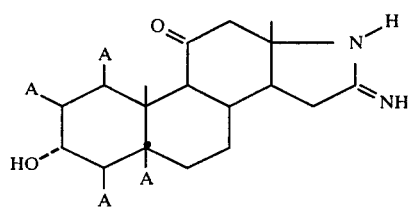

wherein A is selected from the group consisting of hydrogen and tritium comprises reacting a compound of the formula

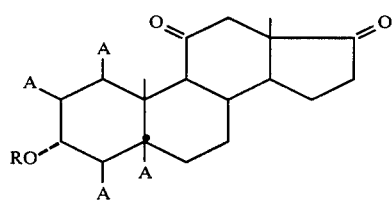

wherein A has the above definition and R is an acyl of an organic carboxylic acid of 1 to 8 carbon atoms with an oximation agent to obtain a compound of the formula

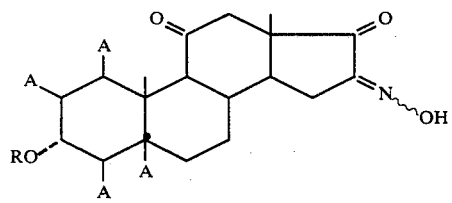

reacting the latter with an agent to form an acid chloride to obtain a compound of the formula

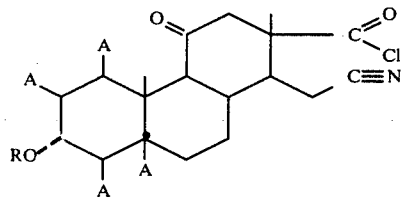

reacting the latter with ammonia to obtain a compound of the formula

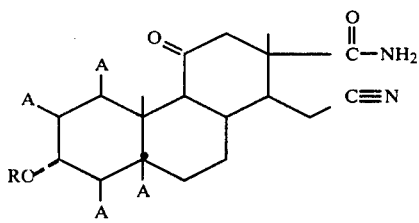

reacting the latter with an alkali metal hypohalite in the presence of a base to obtain a compound of the formula

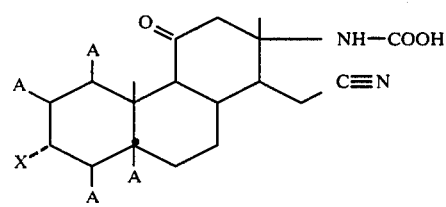

wherein A has the above definition and X is a halogen and reacting the latter with a base to obtain the desired compound of formula I.

Examples of suitable carboxylic acids for the acyl of R are alkanoic acids such as formic acid, acetic acid, propionic acid, butyric acid, isobutyric acid, valeric acid and hexanoic acid but acetic acid is preferred.

The oximation agent is preferably an alkyl nitrite such as tert.-butyl nitrite and the reaction is preferably effected in the presence of a strong base such as potassium tert.-butylate. The acid chloride forming agent is preferably thionyl chloride but other chlorinating agents may be used and the reaction is effected at low temperatures preferably.

The hypohalite with a formula of MOX wherein X is a halogen and M is an alkali metal is preferably sodium hypochlorite and the reaction is effected in the presence of a base such as sodium hydroxide. However, the reaction may also be effected with bromine in the presence of an alkali metal alcoholate such as sodium methylate. The transformation of a compound of formula VI into the compound of formula I is effected in the presence of a base such as sodium hydroxide and is preferably effected at reflux in an organic solvent such as methanol.

In a preferred mode of the process of the invention, A is hydrogen and R is preferably acetyl. The preferred oximation agent is nitrous acid, alkali metal nitrite such as sodium nitrite or a lower alkyl nitrite such as tert.-butyl nitrite or isopentyl nitrite. When a salt of nitrous acid is used, the reaction is preferably effected in the presence of an acid such as a mineral acid like hydrochloric acid or an organic acid such as acetic acid.

When an ester of nitrous acid is used, the reaction is preferably effected in the presence of a strong base such as an alkali metal alkylate like potassium tert.-butylate. The oximation reaction is preferably effected at room temperature or with cooling. The formation of the acid chloride is effected under standard conditions, preferably using thionyl chloride or phosphorus pentachloride.

In a more preferred mode of the process, the oximation is effected with tert.-butyl nitrite in the presence of a strong base and the acid chloride is formed with thionyl chloride and the compound of formula V is reacted with sodium hypochlorite in the presence of sodium hydroxide.

The compounds of formulae III, IV, V and VI are novel intermediate compounds and preferred are those wherein A is hydrogen. The novel compound of formula I wherein A is tritium is novel and is useful as a radioactive marker for the GABA receptor.

The compounds of formula II wherein A is hydrogen and R is acetyl is described in French Pat. No. 942,260 and German Pat. No. 2,062,911 and the compounds wherein R is other than acetyl may be made therefrom by known methods.

The compounds of formula II wherein A is tritium may be prepared by reacting a compound of the formula

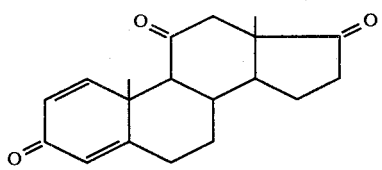

A described in U.S. Pat. Nos. 2,902,498 and 2,902,410 and in German patent DT 2.062.911 with a reactant for protecting the 17-keto group to form a compound of the formula

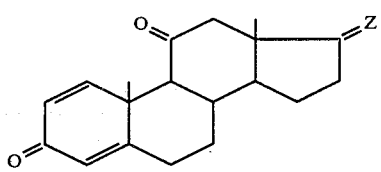

B wherein Z is a keto protective group, reacting the latter with tritium to obtain a compound of the formula

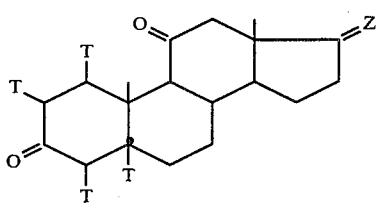

C wherein T is tritium atom, optionally submitting to a separation for recovering the sought 5β-isomer of formula C and reacting the latter with a reducing agent to obtain a compound of the formula

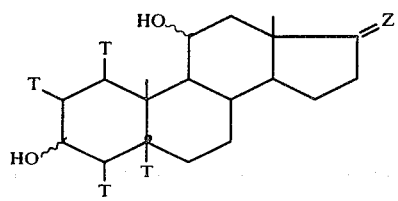

D subjecting the latter to an acylation agent to obtain a compound of the formula

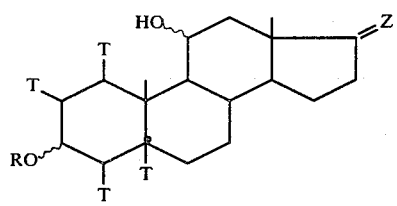

E wherein R has the above definition, optionally submitting to a separation for recovering the sought 3α-isomer and reacting the same with an oxidation agent to obtain a compound of the formula

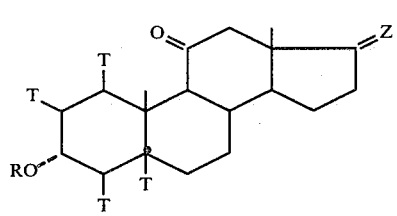

F and reacting the latter with a reagent able to release the 17-keto protective group to form the compound of the formula

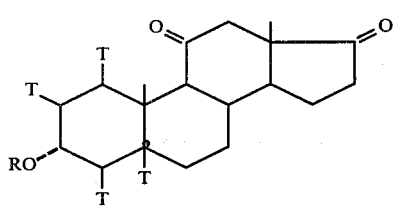

II$_b$

In a preferred mode of the invention, the reagent for forming the 17-keto protective group is ethylene glycol in the presence of p-toluene sulfonic acid and the isomers of formulae C and E are separated by chromatography. The reduction of the compound of formula C is effected with an alkali metal hydride such as sodium borohydride or potassium borohydride and the acylation is effected with acetic anhydride to obtain R as acetyl. The oxidation of the compound of formula E is effected with a mild oxidation agent such as pyridinium chlorochromate and the hydrolysis of the 17-keto protective group is effected with an acid such as hydrochloric acid when >C=Z is a dioxolane group.

At the time of the reaction of the products of formula VI to products of formula I, the product of formula

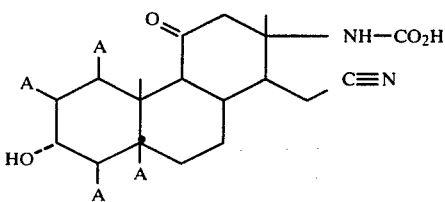

VII may be obtained intermediately but normally this product is not isolated. Certain stages of the process described above may also be carried out without isolation of the intermediate product. In addition, it is possible to pass directly from products of formula III to products of formula V without isolating the product of formula IV.

The products of formula I may be present in two tautomeric forms. In addition to the form described above, there also exists a form of formula $I_Z$ and there is in fact an equilibrium as follows:

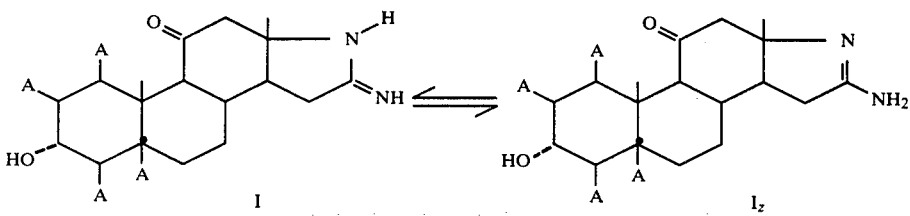

Lastly, the products of formula I contain an amine function and may be present in the form of salts with acids, in particular mineral acids and it has been possible to prepare 16-imino-17-aza-5β-androstane 3α-ol-11-one hydrochloride. Examples of other acids are sulfuric acid, nitric acid, hydrobromic acid, phosphoric acid, etc.

In the following examples there are described several preferred examples to illustrate the invention. However, it should be understood that the invention is not intended to be limited to the specific embodiments.

EXAMPLE 1

16-imino-17-aza-5β-androstane-3α-ol-11-one

STEP A:

3α-acetoxy-16-oximino-5β-androstane-11,17-dione

At ambient temperature, 500 ml of tert.-butyl nitrite were added all at once to a solution of 500 g of 3α-acetoxy-5β-androstane-11,17-dione in 2.5 liters of anhydrous methylene chloride and the solution was adjusted to 0° C. Then, over a period of 30 minutes at 0° and 2° C., a solution of 201 g of potassium tert.-butylate in 1.5 liters of tert.-butanol was added thereto and after stirring for 2 minutes at 0° C., the solution obtained was introduced into 1.835 liters of a solution of N hydrochloric acid in methanol at 0° C. over a period of 45 minutes. The solution was washed 3 times with 2.5 liters of distilled water, dried and evaporated to dryness under reduced pressure at 40° C. The resin obtained was added to 500 ml of ethyl acetate and the mixture was refluxed until dissolved and the solution was cooled and the solvent was evaporated under reduced pressure to obtain 613 g of crystalline product. The latter was triturated 3 times in ether and dried at 40° C. to obtain 405.6 g of 3α-acetoxy-16-oximino-5β-androstane-11,17-dione in the form of white crystals melting at 267° C.

STEP B:

3α-acetoxy-17-chloro-16,17-seco-5β-androstanonitrile-16-11,17-dione

Over 15 minutes, 5 g of the product of Step A were introduced in small amounts into 50 ml of thionyl chloride cooled to 0° C. and the mixture was stirred for 1 hour at about 0° C. and then was evaporated to dryness under reduced pressure at about 40° C. The residue was taken up in methylene chloride and the solution was poured into a mixture of ice and water. The decanted organic phase was washed first with water, then with 5% sodium bicarbonate and finally with water. The wash waters were extracted twice with methylene chloride and the combined organic phases were dried, and evaporated to dryness. The residue was crystallized from isopropyl ether by cooling and filtering. The product was washed with isopropyl ether and dried at 90° C. to obtain 4.58 g of 3α-acetoxy-17-chloro-16,17-seco-5β-androstanonitrile-16-11,17-dione melting at 212° C.

STEP C:

3α-acetoxy-17-amino-16,17-seco-5β-androstanonitrile-16-11,17-dione

At 20° C. and with stirring, 7 ml of 22° Be ammonium hydroxide were added dropwise to a solution of 700 mg of the product of Step B in 21 ml of acetone and after standing for 90 minutes at 20° C., the mixture was poured into water. The mixture was extracted with methylene chloride and the organic phase was washed with water, dried and evaporated to dryness under reduced pressure. The residue was crystallized by concentration in an acetone-isopropyl ether mixture to obtain 615 mg of 3α-acetoxy-17-amino-16,17-seco-5β-androstanonitrile-16-11,17-dione melting at 190° C. and having a specific rotation of $[\alpha]_D^{20} = +57° \pm 2°$ (c=0.6% in chloroform).

STEP D:

3α-chloro-17-aza-17-carboxy-16,17-seco-5β-androstanonitrile-16-11-one

Under nitrogen, a suspension of 45 g of the product of Step C in 1.125 liters of ethanol was cooled to 10° C. and then over a period of 5 minutes, 337.5 ml of N sodium hydroxide were added. After cooling to 0° C., 112 ml of 47°/50° chlorometric "eau de javelle" extract were added dropwise over 15 minutes and the mixture was stirred for 90 minutes at 0° C. The reaction medium was poured into 3.365 liters of iced water and the neutral fractions were extracted three times with 650 ml of methylene chloride. The combined organic phases were re-extracted with 300 ml of water and the combined aqueous phases at 10° and 15° C. were acidified with N hydrochloric acid. The mixture was extracted with methylene chloride and the organic phase was washed with water and evaporated to dryness under reduced pressure at 35° C. The 36.8 g of white crystals were taken up in 40 ml of acetone and 400 ml of isopropyl ether were added. Crystallization was initiated and after standing for a while at 4° C., the mixture was filtered. The product was washed twice with isopropyl ether and dried under reduced pressure to obtain 31.6 g of 3α-chloro-17-aza-17-carboxy-16,17-seco-5β-androstanonitrile-16-11-one melting at 212° C. (decomposition).

STEP E: 16-imino-17-aza-5β-androstane-3α-ol-11-one 68 ml of 10N sodium hydroxide were introduced under nitrogen into a suspension of 31.5 g of 3α-chloro-17-aza-17-carboxy-16,17-seco-5β-androstanonitrile-16-11-one in 600 ml of methanol and after refluxing for one hour, the mixture was cooled to 20° C. The mixture was evaporated to dryness under reduced pressure and the residue was taken up in 350 ml of water. After standing at +4° C., the mixture was filtered and the product was washed with iced water and dried at 40° C. to obtain 15.6 g of 16-imino-17-aza-5β-androstane-3α-ol-11-one melting at 260° C.

EXAMPLE 2

16-imino-17-aza-5β-androstane-3α-ol-11-one hydrochloride

At room temperature, 20 g of 16-imino-17-aza-5β-androstane-3α-ol-11-one in 400 ml of anhydrous methanol was stirred until dissolution occured and while stirring, 27 ml of 2.5N hydrochloric acid in methanol were added dropwise under nitrogen. Then 100 ml of isopropyl ether were added and the mixture was filtered. The product was washed with an isopropyl ether-methanol mixture (1—1) and dried to obtain 14.6 g of 16-imino-17-aza-5β-androstane-3α-ol-11-one hydrochloride. Then, a second lot of 2.7 g were obtained which after crystallization from the mother liquors had a Rf=0.47 (chloroform-methanol 50—50; acetic acid 5%).

Analysis: Calculated: %Cl 10.5 Found: 10.39

Various modifications of the process of the invention may be made without departing from the spirit or scope thereof and it is to be understood that the invention is to be limited only as defined in the appended claims.

What we claim is:

1. A process for the preparation of a 16-imino-17-aza-steroid of the formula

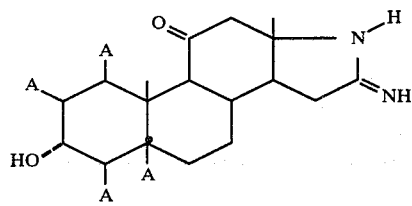

wherein A is selected from the group consisting of hydrogen and tritium comprises reacting a compound of the formula wherein A has the above definition and R is an acyl of an alkanoic acid of 1 to 8 carbon atoms with an alkyl nitrite to obtain a compound of the formula reacting the latter with a chlorinating agent to form an acid chloride to obtain a compound of the formula reacting the latter with ammonia to obtain a compound of the formula reacting the latter with an alkali metal hypohalite in the presence of a base to obtain a compound of the formula wherein A has the above definition and X is a halogen and reacting the latter with a base to obtain the desired compound of formula I.

2. The process of claim 1 wherein A is hydrogen and R is acetyl.

3. The process of claim 1 wherein the oximation agent is tert.-butyl nitrite and the reaction is effected in the presence of a strong base.
4. The process of claim 1 wherein the chlorinating agent is thionyl chloride.
5. The process of claim 1 wherein the alkali metal hypohalite is sodium hypochlorite.
6. A compound of the formula
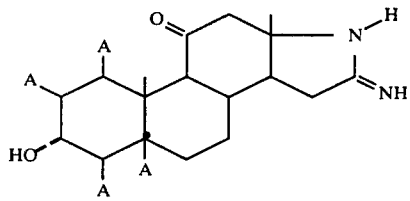
wherein A is tritium.
* * * * *